United States Patent [19]
Chan et al.

[11] Patent Number: 6,096,776
[45] Date of Patent: *Aug. 1, 2000

[54] GREEN PORPHYRINS AS IMMUNOMODULATORS

[75] Inventors: Agnes H. Chan, Port Moody; David W. C. Hunt, White Rock; Julia G. Levy, Vancouver; Modestus O. K. Obochi, Vancouver; Anna M. Richter, Vancouver; Guillermo O. Simkin, Vancouver, all of Canada

[73] Assignees: QLT PhotoTherapeutics, Inc.; The University of British Columbia, both of Canada

[*] Notice: This patent is subject to a terminal disclaimer.

[21] Appl. No.: 09/164,374

[22] Filed: Oct. 1, 1998

Related U.S. Application Data

[63] Continuation-in-part of application No. 08/856,921, May 16, 1997, Pat. No. 6,008,241, which is a continuation-in-part of application No. 08/374,158, Jan. 17, 1995, Pat. No. 5,789,433.

[51] Int. Cl.[7] .................................................. A61K 31/40
[52] U.S. Cl. ............................................................. 514/410
[58] Field of Search ............................................. 514/410

[56] References Cited

U.S. PATENT DOCUMENTS

| | | |
|---|---|---|
| 4,883,790 | 11/1989 | Levy et al. . |
| 4,920,143 | 4/1990 | Levy et al. . |
| 5,095,030 | 3/1992 | Levy et al. . |
| 5,171,749 | 12/1992 | Levy et al. . |
| 5,283,255 | 2/1994 | Levy et al. . |
| 5,422,362 | 6/1995 | Vincent et al. . |
| 5,484,804 | 1/1996 | Achard et al. . |

FOREIGN PATENT DOCUMENTS

| | | |
|---|---|---|
| 0 284 409 | 9/1988 | European Pat. Off. . |
| WO 91/12801 | 9/1991 | WIPO . |
| WO 9/03797 | 2/1995 | WIPO . |
| WO 96/21466 | 7/1996 | WIPO . |
| WO 96/22090 | 7/1996 | WIPO . |
| WO 97/09043 | 3/1997 | WIPO . |

OTHER PUBLICATIONS

Mathews–Roth, M.M. "Porphyrin photosensitization and carotenoid protection in mice,; in vitro and in vivo studies" *Chemical Abstracts* 101(15)(1984) Abstract No. 125996.

Richter, A.M. et al, "Photodynamic treatment with BPD–MA (verteporfin) activated with light within difference spectral ranges" *Proc. SPIE–Int. Soc. Opt. Eng.* 3191:15–24 (1977).

Taylor, P.W. "Liposomal Delivery of Photosensitizers" Abstract, *J. Liposome Res.* 6(1):185 (1996).

Bae, J. et al., *J. Invest Dermatol.* (1996) 106:950.

Elmets, C.A. et al., *Cancer Res.* (1986) 46:1608–1611.

Gruner, S. et al., *Scand. Journal Immunol.* (1985) 21:267–273.

Gruner, S. et al., *Tissue Antigens* (1986) 27:147–154.

Hunt, D.W.C. et al., *Immunopharmacology* (1993) 26(3):203–212.

Hunt, D.W.C. et al., *Proceedings of SPIE* (1997) 2972:110–121; Proceedings of Association Internationale de Photobiologie, Vienna, Austria 1996.

Leong, S. et al., *Photochem. Photobiol.* (1996) 64:751–757.

Levy, J.G., *Seminars in Oncology* (1994) (Suppl. 21(6)) 15:4–10.

Levy, J.G., *Stem Cells* (1995) 13(4):336–343.

Simkin, G. et al., Proceedings of Optical Methods for Tumor Treatment and Detection: Methods and Techniques in Photodynamic Therapy IV—*SPIE The International Society for Optical Engineering,* San Jose, CA, Feb. 4–5, 1995, 2392:23–33.

*Primary Examiner*—John M. Cooney, Jr.
*Attorney, Agent, or Firm*—Morrison & Foerster

[57] ABSTRACT

Green porphyrins act as antigen-specific immunomodulators in the active phase of an immune response to a particular antigen, as well as to interfere with intercellular communication. These effects occur in the absence of radiation absorbed by the green porphyrin.

14 Claims, 6 Drawing Sheets and

Overlap BPD-RGD from Group A

Overlap BPD-RGD from Group B

Overlap BPD-RGD from Group C

GREEN PORPHYRINS AS IMMUNOMODULATORS

The present application is a continuation-in-part of U.S. application Ser. No. 08/856,921, filed May 16, 1997 now U.S. Pat. No. 6,008,241, which is itself a continuation-in-part of U.S. application Ser. No. 08/374,158, filed Jan. 17, 1995, now U.S. Pat. No. 5,789,433. The complete text of the Ser. No. 08/374,158 application is incorporated by reference herein, as if fully set forth.

TECHNICAL FIELD

The invention is in the field of modulating immune responses by administering green porphyrins in the absence of light. Antigen-specific immune responses are modulated when the green porphyrins are administered during the course of the response to a specific antigen. In addition, green porphyrins in the absence of light interfere with intercellular communication, thus permitting prevention or treatment of, for example, restenosis.

BACKGROUND ART

A group of compounds useful in photodynamic therapy, collectively designated green porphyrins, is disclosed in a series of patents including U.S. Pat. Nos. 5,283,255; 4,883,790; 4,920,143; 5,095,030; and 5,171,749, the disclosures of which are incorporated herein by reference. These green porphyrins are prepared using a Diels-Alder reaction with hematoporphyrin and optional rearrangement or reduction of the resulting product. A particularly preferred form of these green porphyrins, as outlined in the above-referenced patents, is designated a benzoporphyrin derivative in the monoacid form, or "BPD-MA". This drug is currently in clinical trials with respect to photodynamic treatment of various tumors and other conditions.

Photodynamic therapy rests on the assumption that the photoactive compounds administered, in this case the green porphyrins, are without physiological effect in the absence of light. However, when irradiated, the excited forms of the compounds exert local toxic effects. Therefore, for the treatment of tumors, for example, advantage has been taken of the tendency of these photoactive compounds to be retained in tumor tissue after clearance from normal tissue has been effected. It has also been found that local irradiation to areas of neovasculature is effective even before the compounds have been cleared from normal tissue.

It has now been found that the green porphyrins have immunomodulating activity and interfere with intercellular communication independent of their ability to behave as photoactive agents in PDT. The present invention takes advantage of this property, hitherto unexpected, of the green porphyrins.

DISCLOSURE OF THE INVENTION

The invention takes advantage of the ability of green porphyrins, without irradiation, to participate in an immune response generated with respect to a particular antigen. The resulting immunomodulation is antigen-specific, as is illustrated hereinbelow using results obtained in the delayed-type hypersensitivity reaction. Therefore, the subject can be protected against unwanted responses with respect to autoantigens, allergens and the like without the disadvantage of being immunocompromised generally. In addition, the green porphyrins interfere with intercellular communication such as that which results in thrombosis as illustrated hereinbelow. The green porphyrins are also shown to have conformational similarity to known integrins characterized by the sequence RGD. This permits use of the green porphyrin to prevent or treat conditions characterized by unwanted intercellular communication.

Thus, in one aspect, the invention is directed to a method to modulate an antigen-specific immune response, which method comprises administering to a subject who is experiencing an activated immune response to an antigen, an amount of green porphyrin effective to modulate said immune response to the antigen, in the absence of light absorbed by the green porphyrin, wherein said administering is during the active phase of the immune response to the specific antigen per se.

In another aspect, the invention is directed to a method to modulate intercellular communication in a subject, which comprises administering to a subject in need of such modulation, an amount of green porphyrin effective to modulate the intercellular communication in the absence of light absorbed by the green porphyrin, said administering being performed during the course of the unwanted intercellular communication.

In other aspects, the invention includes formulations of green porphyrins useful in the method of the invention.

MODES OF CARRYING OUT THE INVENTION

There are numerous instances in which an immune response to a particular antigen is undesirable. Prominent among these situations are allergic responses, autoimmune responses, and immune rejections of organ transplants, skin grafts and the like. The green porphyrins of the invention are effective when administered in the active phase of eliciting an immune response, and are thus effective when administered in the time period following exposure to the antigen, or if the immune response in its active form is continuous, during this continuous phase.

The green porphyrins exert their effects in the absence of radiation absorbed by them. By this phrase is meant that no deliberate radiation of the target is employed. Minimal background light may still be present. As described in the Background section above, green porphyrins have been used extensively in photodynamic therapy protocols. In these protocols, a group of cells or a tissue modified to contain substantial amounts of the green porphyrin is deliberately irradiated with light including wavelengths absorbed by the green porphyrin compounds. The absorption of these wavelengths by the green porphyrins results in excitation of the molecules in such a way that surrounding materials are damaged. It is assumed that singlet oxygen is generated in the course of decay of the excited compounds which accounts for the toxicity. The photoactive agent itself, is presumed to be nontoxic.

In the methods of the Present invention, irradiation with light to effect excitation is not, included in the protocol. There is no necessity, however, to block out all light from the subject being treated. Thus, as used herein, the phrase "in the absence of radiation absorbed by the green porphyrin" refers to typical ambient conditions rather than total darkness. It simply indicates that the known photodynamic effects of the green porphyrins are not employed in the methods of the invention.

Green Porphyrins

Figure 1:
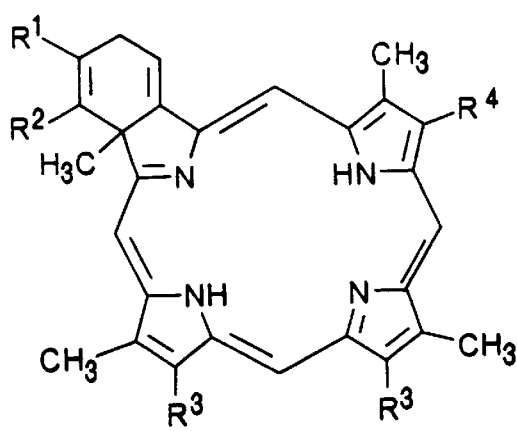
FIG. 1 shows representative structures for the green porphyrins useful in the methods of the invention.

The nature of the green porphyrins is described in the patents referenced in the Background section hereinabove. Briefly, these are derivatives of protoporphyrin IX that are obtainable using a Diels-Alder reaction with a substituted acetylene, optionally followed by rearrangement and/or reduction. Typical formulas for the compounds thus obtained are shown ire FIG. 1. Preferred embodiments of the formulas shown in FIG. 1 are those wherein the ring system has the formulas shown in FIGS. 1–3 or 1–4; and/or wherein each of $R^1$ and $R^2$ is independently selected from the group consisting of carbalkoxyl (2–6C), alkyl (1–6C), arylsulfonyl (6–10C), cyano; and —$CONR^5CO$ wherein $R^5$ is aryl (6–10C) or alkyl (1–6C); each $R^3$ is independently carboxyl, carboxyalkyl (2–6C) or a salt amide, ester or acylhydrazone or is alkyl (1–6C); and $R^4$ is —$CH=CH_2$ or —$CH(OR^{4'})CH_3$ wherein $R^{4'}$ is H, or alkyl (1–6C) optionally substituted with a hydrophilic substituent. Of course, mixtures can be used.

Particularly preferred are those compounds of FIGS. 1–3 and 1–4 wherein each of $R^1$ and $R^2$ is independently carbalkoxyl (2–6C); one $R^3$ is carboxyalkyl (2–6C) and the other $R^3$ is the ester of a carboxyalkyl (2–6C) substituent; and $R^4$ is —$CH=CH_2$ or —$CH(OH)CH_3$.

Figures 1, 2:
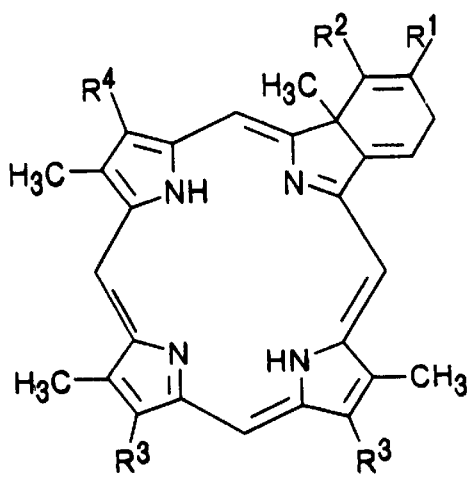
FIG. 2 shows the superimposed conformation of the family of conformations represented by RGDA.
Figures 1, 2, 3:
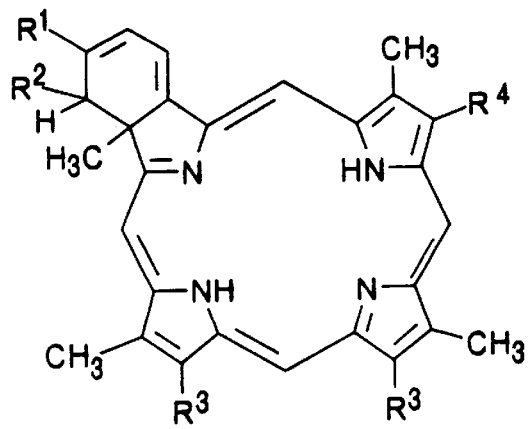
FIG. 3 shows the superimposed conformation of the family of conformations represented by RGDB.

Especially preferred is the compound shown as FIGS. 1–3 wherein $R^1$ and $R^2$ are methoxycarbonyl; one $R^3$ is —$CH_2CH_2COOH_3$ and the other $R^3$ is —$CH_2CH_2COOH$; and $R^4$ is —$CH=CH_2$. This latter compound is referred to as BPD-MA, an acronym for benzohydroporphyrin derivative monoacid wherein the Diels-Alder addition occurs on ring A.

Nature of the Conditions Treated

The green porphyrins, when administered to a vertebrate subject during the course of an activated immune response to a particular antigen, modulate the response to the specific antigen without resulting in any overall immunosuppression. The timing of administration is facilitated if the subject is naive with respect to the immunogen/antigen administered. Unwanted immune responses to deliberately administered antigens are found, for example, in transplantation protocols using allografts, such as skin transplants or organ transplants, individual cellular transplants, such as those used in insulin replacement for diabetes, and any other surgical procedure or procedure involving injection wherein foreign cells or tissues are deliberately introduced into the subject. Other instances where an unwanted immune response may occur to a deliberately administered compound include those wherein proteins of species xenogeneic to those of the subject are used. A typical example is the administration of monoclonal antibodies in the treatment of tumors. In many cases, although attempts at humanizing antibodies have been made, monoclonal antibodies derived from mice are used in human therapy. An undesired immune response to such antibodies can be modulated by the methods of the invention. In these instances, a primary immune response is activated and the administration of green porphyrins contemporaneously with or immediately following the administration of the antigen provides the desired effect.

Another instance wherein an immune response occurs to a foreign antigen, is illustrated by allergic reactions. While these responses are generally secondary immune responses, administration of the green porphyrins of the invention simultaneously with this secondary exposure, or in a time period proximal thereafter, is also effective.

In both of the foregoing cases, the green porphyrin will be administered at the same time that the antigen or allergen is administered or within the time period required for the active response to the antigen. In general, this time period is within 24–48 hours of the administration of antigen.

The subjects for whom the methods of the invention are appropriate are generally vertebrate subjects, preferably mammalian subjects. However, vertebrate organisms generally utilize similar intercellular communication systems and assemble immune responses in analogous ways. Particularly preferred subjects are domesticated animals and avian subjects, as well as human subjects. The appropriate protocols, dosage, and formulation will depend, of course, on the nature of the subject.

Administration of the Antigen

The administration of the antigen simultaneously with or proximally before the administration of the green porphyrin will vary depending on the nature of the allergin. For deliberately administered antigens, such as drugs, monoclonal antibodies or other foreign proteins which are used for therapeutic or diagnostic purposes, the dosage level and form of administration will be controlled by the purpose for which the antigen is administered generally. The antigen is typically already available in a suitably formulated pharmaceutical composition and the dosage levels and expected routes of administration are already known.

With respect to allografts, it is generally believed that the cells that define tissues or organs from members of the same species as the intended recipient, including vascularized organs such as the heart, kidney, liver, lungs, etc. and endocrine glands such as pituitary, thyroid, adrenal, parathyroid and pancreas and skin grafts, while immunogenic, may not contain the major histocompatibility antigen that trigger rejection of the transplant. Rather, these antigens are believed to be carried by passenger cells such as leukocytes that are included in the transplanted cells as impurities.

Thus, the administration of the green porphyrin can either be performed at the time of, or approximately after, the transplant itself carrying the MHC-bearing cells, or the subject may be protected in advance by administering the relevant histocompatibility antigens separately, either as proteins per se, or included on the surfaces of cells bearing them. The green porphyrin is then administered at a time proximal to the preadministration of the cells or histocompatibility antigens. For example, a major determinant of histocompatibility in humans is designated HLA-DR in the group of MHC Class II antigens. These have been subclassified, and if the donor has been typed, the subtype of DR antigen can be administered along with proximal administration of the green porphyrin prior to the transplant per se.

If the antigen is an allergen, the allergen can be administered directly by injection or orally along with the green porphyrin or immediately prior to administration of the green porphyrin. Alternatively, the administration may mimic natural exposure by placing the subject in proximity to, for example, plants which contain pollen known to elicit an allergic response in the subject. When the subject is placed in this environment, green porphyrin is administered simultaneously or very soon thereafter.

If the antigen is an autoantigen, such as believed responsible for a number of conditions including rheumatoid arthritis, multiple sclerosis, lupus erythematosus, certain types of diabetes, or inflammatory reactions generally caused by an autoantigen, the administration of the antigen cannot separately controlled. The efficacy of the method of the invention depends on the continuing active immune response to the autoantigen which is supplied internally. In this case, the green porphyrin is administered to the subject afflicted with the autoimmune disease, preferably during episodes when the immune response is most evident.

An additional condition believed to be related to an autoimmune response is psoriasis. The method of the invention is suitable, especially using topical administration, for treatment of this condition.

Intercellular Communication

In addition to it ability to modulate an immune response, the green porphyrins of the invention are able to interfere with intercellular communication putatively by virtue of their similarity in form to the integrins. As shown hereinbelow, the three-dimensional structure of the green porphyrins of the invention mimics the three-dimensional structure of the favored conformations representative of molecules containing the adhesion sequence RGD. Further, it is demonstrated that the green porphyrins are able to interrupt thrombosis, a known capacity of the RGD-based compounds. Therefore, the methods of the invention are also suitable for the treatment of conditions where intercellular communication has negative effects on the subject.

One such instance is in the formation of restenoses following surgery or other traumatic disturbance of the vasculature. For this purpose, the method of the invention can be employed proximal to surgical procedures representing risks of formation of blood clots in response to this stress. The administration will typically be systemic and timed so as to effect interruption of the required cellular communication responsible for thrombosis.

Formulation and Administration

The green porphyrins of the invention may be formulated and administered in a manner convenient generally for small-molecule drugs as is known in the art, for example, as set forth in *Remington's Pharmaceutical Sciences*, Mack Publishing Company, Easton, Pa., Latest Edition. The composition will contain a quantity of the green porphyrin effective to provide immunomodulation or interruption of intercellular communication. The dosage level will vary depending on the mode of administration, formulation, condition to be treated, and the nature of the subject; however, in general, the amount of green porphyrin for systemic administration is of the order of 10 $\mu$g/kg to 100 mg/kg, preferably 100 $\mu$g/kg–10 mg/kg, and most preferably around 1 mg/kg. If administration is topical, suitable concentrations in the composition ranging from about 5% to about 95% of the composition, preferably about 10%–50% of the composition are employed.

Routes of systemic administration can be by intrajection, including intravenous, intramuscular, intraperitoneal and the like; oral, transmucosal or transdermal using appropriate excipients, and the like. Localized administration can be achieved also by transdermal or transmucosal means using suppositories or skin patches or the green porphyrins may be applied topically in the form of gels or salves.

When systemic administration is employed, liposomal compositions are particularly preferred. Liposomes can be prepared using standard methods; they typically are prepared from negatively charged phospholipids such as phosphatidyl glycerol, phosphatidyl serine or phosphatidyl inositol as well as lipids per se and various stabilizing agents. The liposomes may be multilamilar or monolaminar and are in a range of sizes. The concentration of green porphyrin in the liposomal composition is typically on the order of 1–20%.

The following examples are intended to illustrate but not to limit the invention.

EXAMPLE 1

Effect on MBP-Induced EAE

Experimental allergic encephalomyelitis (EAE) in PL mice has been used as a model for multiple sclerosis in humans. This condition can be induced by injecting splenocytes from donor mice primed with a myelin basic protein (MBP). Splenocytes were obtained as follows: PL mice were administered 0.1 ml of a mixture prepared by emulsifying MBP (4 mg/ml phosphate-buffered saline) in an equal volume of complete Freund's adjuvant (4 mg of *Mycobacterium tuberculosis* H37RA in incomplete Freund's adjuvant). Mice were injected subcutaneously at the tail base. Ten days following immunization, spleens were removed and teased into single cell suspensions. Cells were pelleted by centrifugation and erythrocytes removed by lysis in 0.14 M $NH_4Cl$. Cells ($4\times10^6$/ml) were cultured in RPMI 1640 medium containing 5% fetal calf serum, $5\times10^{-5}$ M 2-mercaptoethanol, 1 mM sodium pyruvate, 20 mM HEPES, 2 mM 1-glutamine, 100 U/ml penicillin, 100 $\mu$g/ml streptomycin and 100 $\mu$g/ml MBP in 75 $cm^2$ flasks. Following three days at 37° C., 5% $CO_2$ the cultures were pulsed with human recombinant interleukin-2 (rIL-2, 50 U/ml) and returned to the incubator for a further 48 hours. Cells were then harvested, washed with serum-free medium and $5\times10^7$ cells injected intravenously (iv) into naive, syngeneic animals. Mice thus treated typically developed EAE with 18–25 days post-cell transfer.

Four control mice were injected intravenously with $5\times10^7$ of the cells prepared and cultured as described in the preceding paragraph. After 19–30 days, three of the four mice developed the characteristic paralytic disease associated with EAE. This condition is induced when MBP-reactive T lymphocytes invade the central nervous system. However, in the experimental group, four mice, similarly injected with MBP-primed and cultured cells, were administered 1.0 mg/kg BPD-MA intravenously 24 hours later. None of these mice developed the EAE condition. However, mice administered the same dose of BPD 24 hours prior to the injection of the MBP-primed and cultured cells, showed the same course of EAE as did the controls.

Since BPD-injection was effective only when administered within about 24 hours after administration of the cultured cells, BPD is shown to act directly on the transferred activated T cells, rather than on the endogenous cells of the recipient animals.

Splenocytes prepared as described in paragraph 1 of this example, when cultured with 100 $\mu$g/ml of MBP, generate a proliferative response by expansion of T cells specific for, and activated by, MBP. This proliferative response is indexed at 100% in comparison with cells cultured in the absence of MBP which is indexed at 0%. When the cells are cultured in the presence of BPD at concentrations of 1 ng/ml–1 $\mu$g/ml, the proliferation is inhibited. At 1 ng/ml of BPD the proliferation is only 20%; the index falls to zero at 10 ng/ml. At over 100 ng/ml, the proliferative response is less than that seen in the cells cultured in the absence of MBP.

It is known that BPD at the concentration range used has no innate toxicity in the absence of light; therefore, these results suggest that BPD induces anergy in MBP-specific T cells.

EXAMPLE 2

Effect of BPD on DTH

The well documented delayed-type hypersensitivity (DTH) model was employed. Dinitrofluorobenzene (DNFB) was painted onto the inguinal area of hairless strain mice on day 0. On day 5, the DNFB is painted onto the ear, resulting in significant inflammatory response, including swelling of the ear, during the following 24 hours orchestrated by antigen-specific T cells.

Mice painted with DNFB on day 0 were injected intravenously with liposomal BPD-MA at a dose of 1 mg/kg on day −2, −1, 0, +1, +3 or +4. On day 5 the mice were challenged by painting DNFB onto the ear and ear swelling was measured 24 hours later. Minimal ear swelling was noted in unprimed mice. DNFB-sensitized mice administered saline rather than BPD showed a strong ear-swelling response following challenge with DNFB. Swelling was recorded as percent swelling, or $$\frac{\text{ear thickness post-challenge minus ear thickness pre-challenge}}{\text{ear thickness pre-challenge}} \times 100$$

Swelling was usually in the range of 60–90% above control levels. However, when BPD was given on days −2, −1, 0, +1, or +3, ear swelling was less than 50% of that observed in the control animals. Inhibition of the DTH response was approximately 25% when BPD was given on day 4.

In an additional experiment, mice that had been previously sensitized with DNFB were treated with a different skin contact sensitizer, oxazolone. The mice were subsequently challenged with DNFB and oxazolone. Mice treated with BPD showed suppression of the response to DNFB. However, no diminution in the ear swelling in response to oxazolone was found in mice administered BPD. Thus, only the antigen-specific T cells (reactive to DNFB) were affected by BPD. The mice retained their ability to respond to the second antigen, oxazolone, despite the treatment with BPD in conjunction with DNFB sensitization.

EXAMPLE 3

Effect of BPD on Fibrinogen Binding

Platelets were activated by thrombin according to a modification of the method of Shattil et al. *Blood* (1987) 70:307. Briefly, after a 15-minute preincubation at 22° C. with 100 μg/ml liposomal BPD or control, citrated whole blood was treated with α-thrombin (10 U/ml final concentration) in the presence of the fibrin polymerization inhibitor Gly-Pro-Arg-Pro (1.25 mM final concentration) for 30 minutes at 22° C. Platelet activation was measured by assessing bound fibrinogen using fluorescein-labeled antifibrinogen polyclonal antibodies in a flow cytometric analysis. The results are shown in Table 1 as the percentage of platelets positive for antifibrinogen (determined as the mean of three experiments plus or minus one standard deviation).

TABLE 1

PERCENTAGE PLATELETS POSITIVE FOR ANTI-FIBRINOGEN
Mean of 3 ± (1 S.D.)

|  | BPD-Liposomes | Liposomes | No Treatment |
|---|---|---|---|
| No agonist | 2.9 | 2.1 | 2.2 |
|  | (0.8) | (2.5) | (2.2) |
| Thrombin | 28.9 | 86.7 | 86 |
|  | (2.0) | (1.3) | (2.2) |

As seen in Table 1, when treated with thrombin the percentage of platelets positive for antifibrinogen rises from about 2% to about 86–87% when BPD is absent. However, when 100 μg/ml of liposomal BPD is present, the level of activation is diminished by about two-thirds.

EXAMPLE 4

Effect of BPD on Skin Allograft Rejections

The skin allograft rejection assay involving skin grafts between MHC-incompatible mice was conducted according to the method of Billingham et al., "The Technique of Free Skin Grafting in Mammals", *J. Exp. Biol.*, 28:385–402 (1951). Control mice (n=16) reject the grafts at day 11.1±1.9 following allograft.

In the experimental group, (n=6) mice received a single intravenous injection of 0.25 mg/kg BPD-MA liposomal preparation 3–4 hours after allografting and showed prolonged engraftment of 20.7±0.9 days to rejection. Another group of mice who received an additional 0.25 mg/kg injection of BPD on day 8 showed a median rejection time of 23.3±1.9 days.

Thus, BPD without irradiation appears to suppress rejection of allografts.

EXAMPLE 5

Effect of BPD on Adhesion Molecules in Rheumatoid Arthritis

The cell surface adhesion molecule ICAM-1 is upregulated in activated cells. Therefore, appearance of this molecule is considered an indicator of cellular activation.

Synovial fluids from patients with rheumatoid arthritis were incubated in tissue culture medium for 18 hours with varying concentrations of BPD, treated with anti-ICAM-1 and subjected to flow cytometry. The results of this assay are shown in Table 2.

TABLE 2

| (BPD) | Ungated Cell Population | | Lymphocytes | | Monocytes | | PMNs | |
|---|---|---|---|---|---|---|---|---|
| ng/ml | MED | +VE | MED | +VE | MED | +VE | MED | +VE |
| 0 | 24.4 | (85.7%) | 14.2 | (23.7%) | 478 | (85.9%) | 20.4 | (99.3%) |
| 15 | 26.7 | (87.7%) | 13.6 | (30.7%) | 509 | (95.9%) | 22.0 | (99.3%) |
| 25 | 26.7 | (87.0%) | 14.6 | (29.1%) | 496 | (93.8%) | 21.9 | (99.5%) |
| 50 | 23.9 | (84.5%) | 12.9 | (23.5%) | 443 | (94.2%) | 20.0 | (99.2%) |
| 100 | 14.9 | (66.9%) | 13.7 | (22.7%) | 309 | (46.6%) | 12.5 | (69.0% |

+VE: Percentage of cells positive for ICAM-1.
MED: Median value of fluorescence intensity of cells expressing ICAM-1.

As shown in Table 2, the percentage of ungated cells positive for ICAM-1 decreases from 85.7% in the absence of BPD to 66.9% in the presence of 100 ng/ml BPD. The percentage of lymphocytes displaying this molecule was relatively unaffected by BPD; however, for monocytes and polymorphonuclear cells, 100 ng/ml BPD significantly reduced the expression of ICAM-1.

Without wishing to be bound by any theory, applicants believe that the antigen-specific immunomudulation exerted by BPD in the dark results from its interaction with integrins or adhesion molecules expressed on activated hematopoietic cells so as to disrupt cellular communication.

EXAMPLE 6

Relation of BPD-MA to Conformation of Integrin-Binding Compounds

Two known integrin antagonists, RGDS and acetylated/amidated CNPRGDYC (wherein tyrosine is present as the methyl ether) were compared with respect to three-dimensional structures to the three-dimensional structure of BPD-MA. This comparison was done by the Alberta Peptide Institute.

Three-dimensional structure predictions for RGDS showed 1584 possible conformations which could be grouped into seven families according to their energies. Predictions with respect to the acetylated, amidated peptide CNPRGDYC provided 1347 conformations grouped into five families according to energies.

A subset of the major family groups in the predictions for both peptides are similar to three groups of conformations that are found experimentally, designated RGDA, RGDB and RGDC. These three groups of conformations were used as representative conformations for both peptides.

Figures 1, 2, 3, 4:
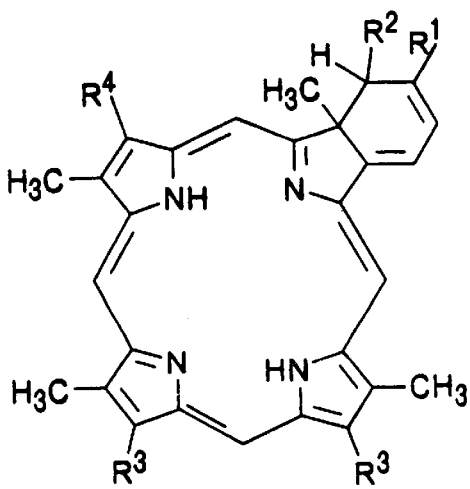
FIG. 4 shows the superimposed conformation of the family of conformations represented by RGDC.
Figures 1, 2, 3, 4, 5:
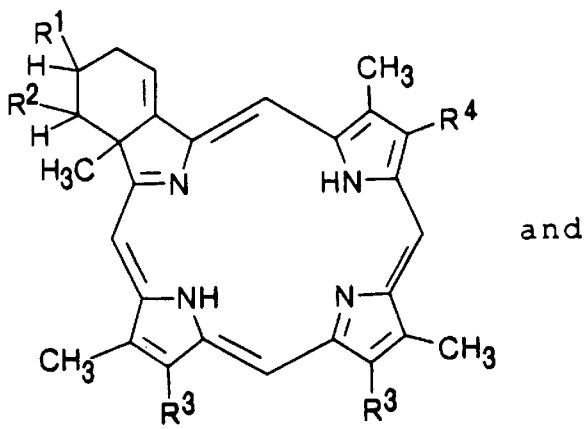
FIG. 5 shows the superimposition of the three-dimensional structure of BPD-MA with a representative conformation of RGDA.
Figures 1, 2, 3, 4, 5, 6:
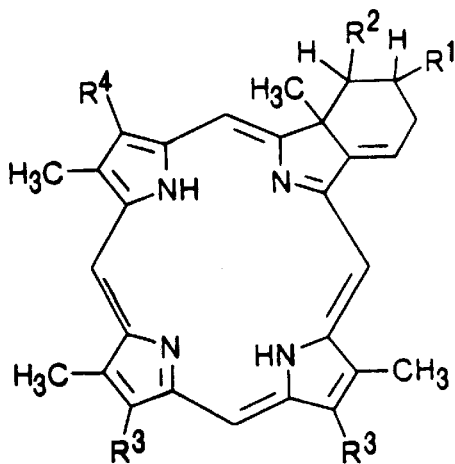
FIG. 6 shows the superimposition of the three-dimensional structure of BPD-MA with a representative conformation of RGDB.
Figure 2:
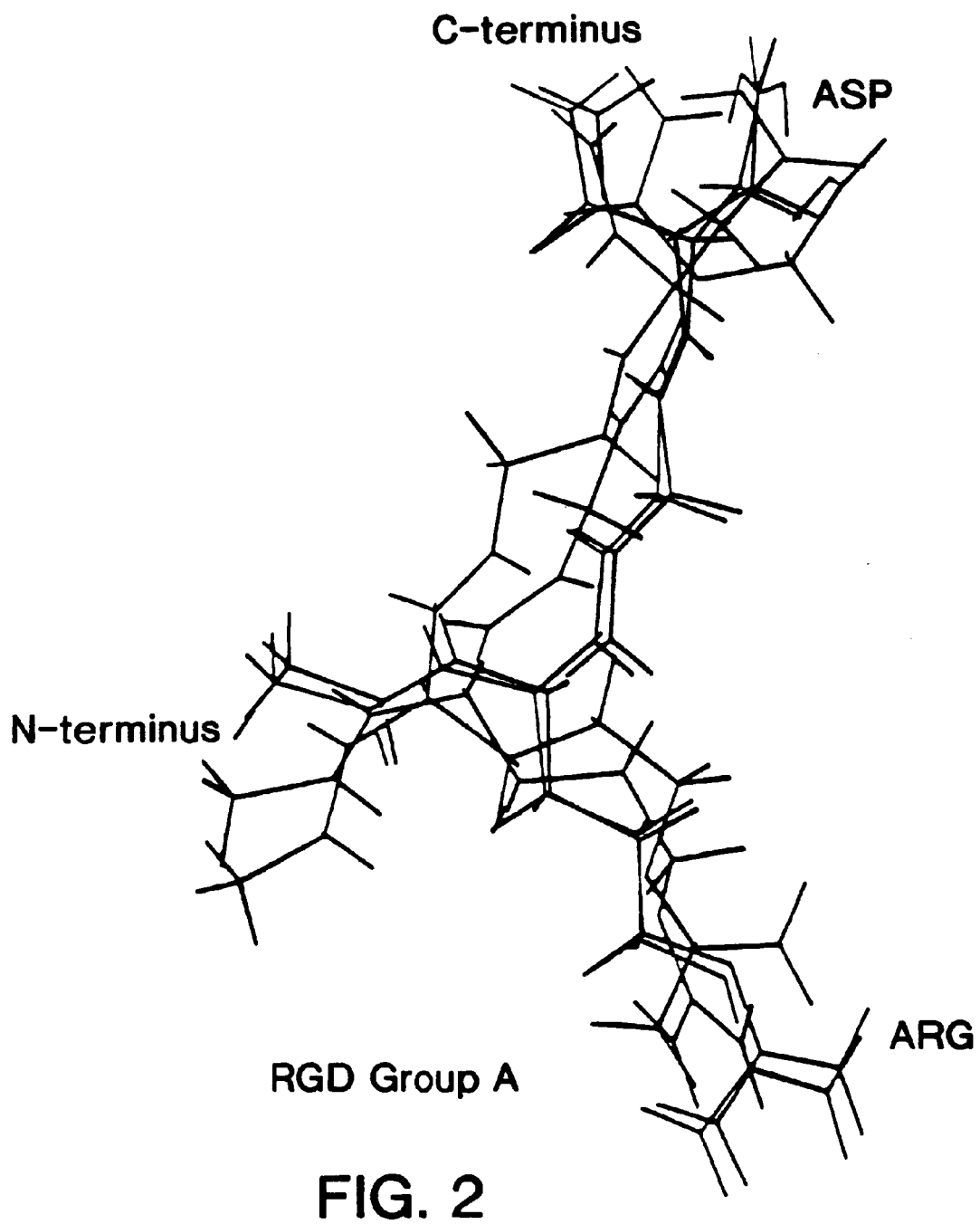
Figure 3:
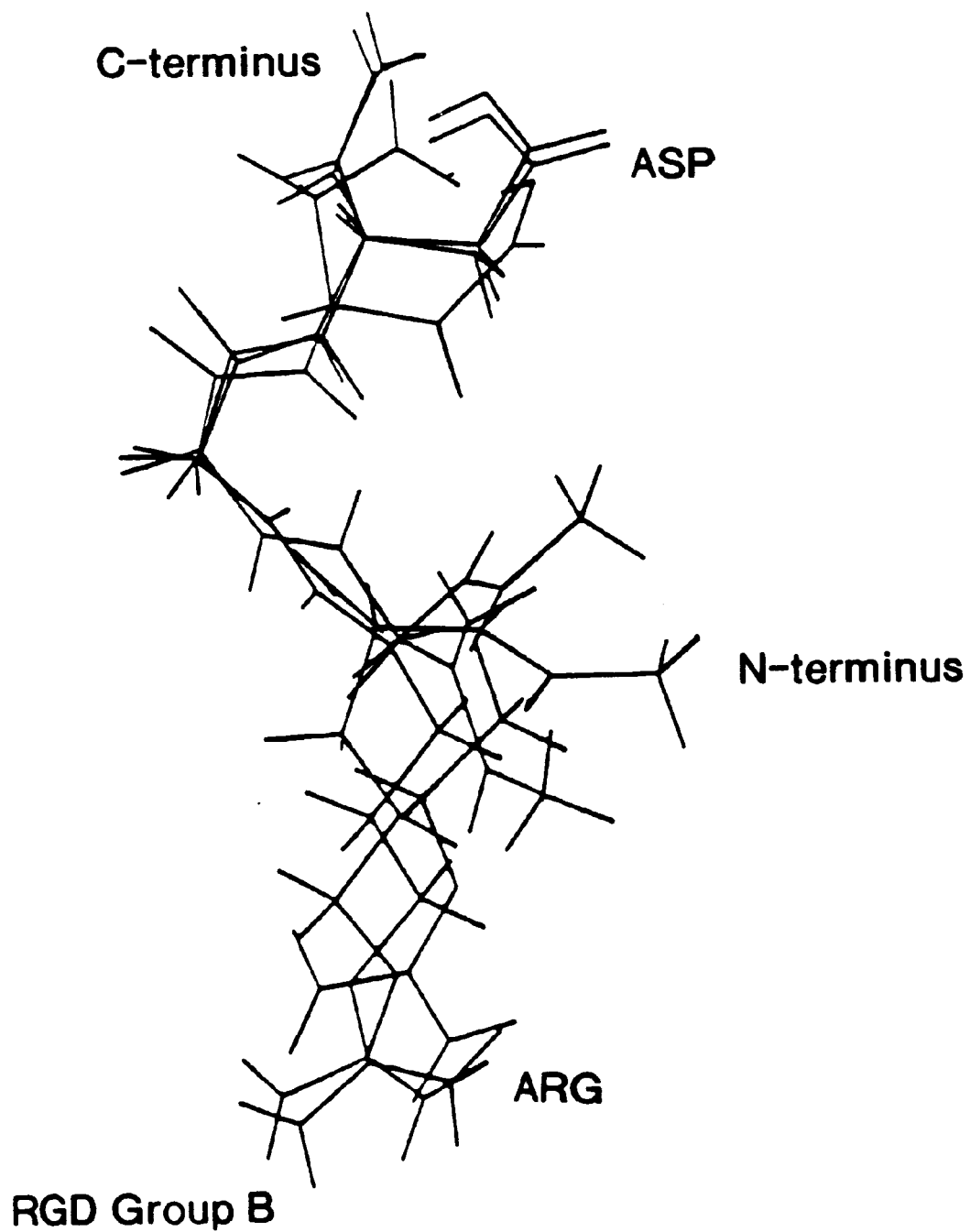
Figure 4:
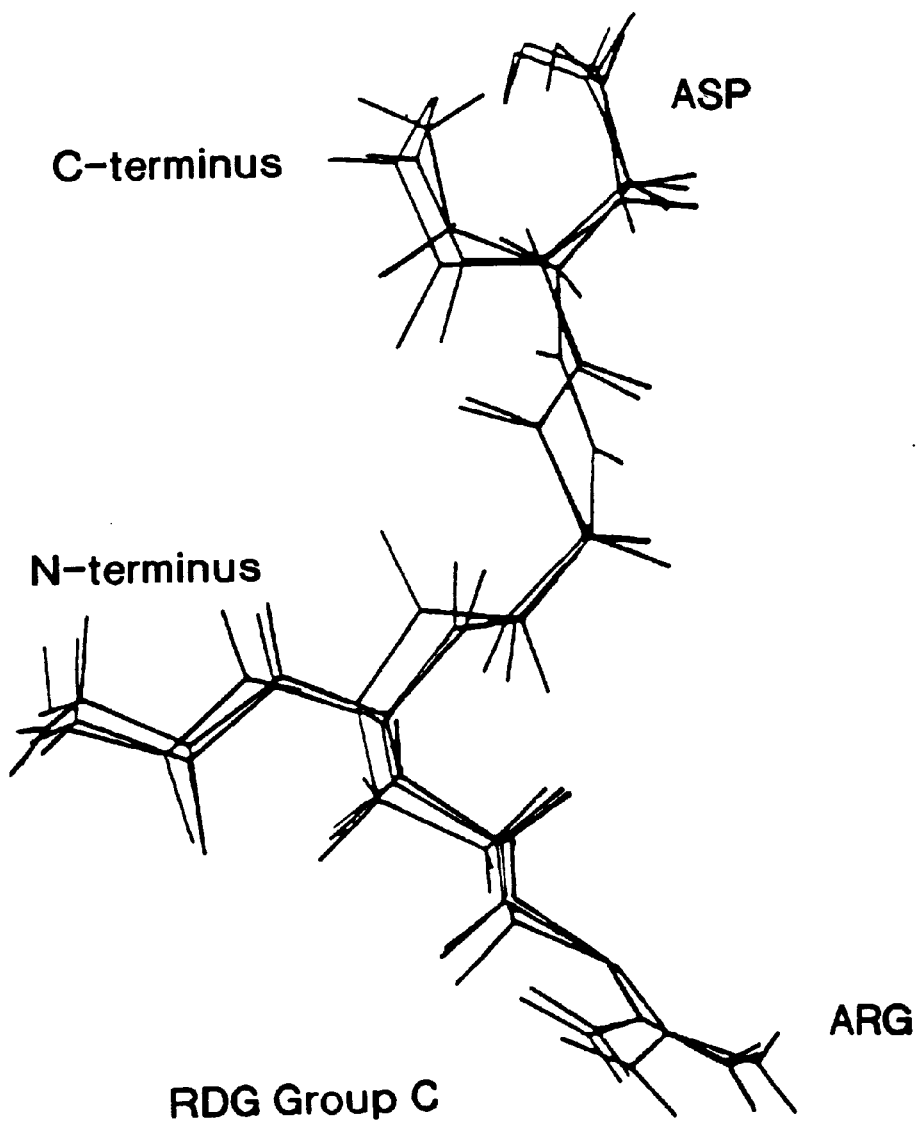
Figure 5:
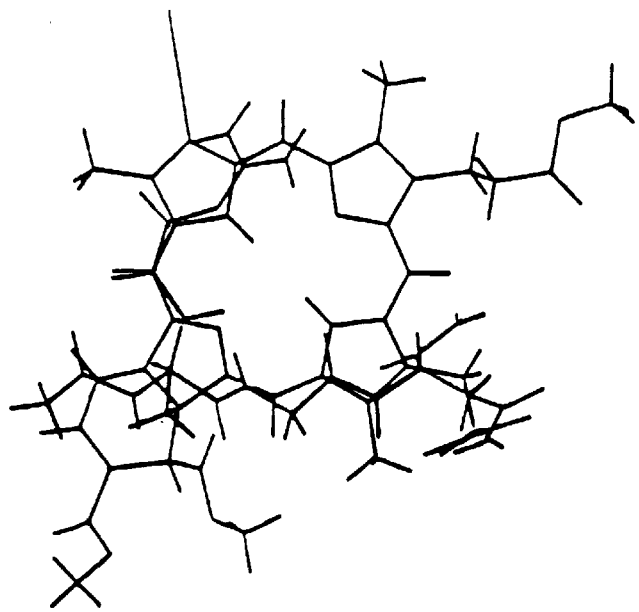
Figure 6:
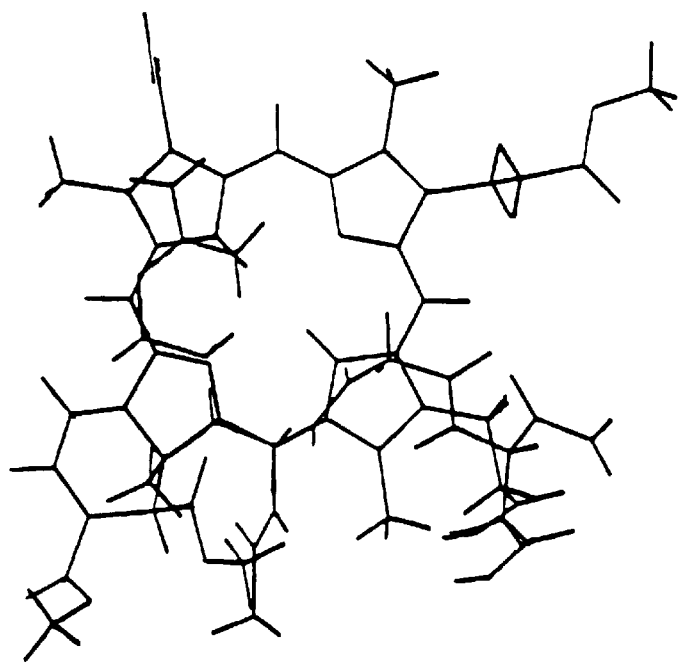
Figure 7:
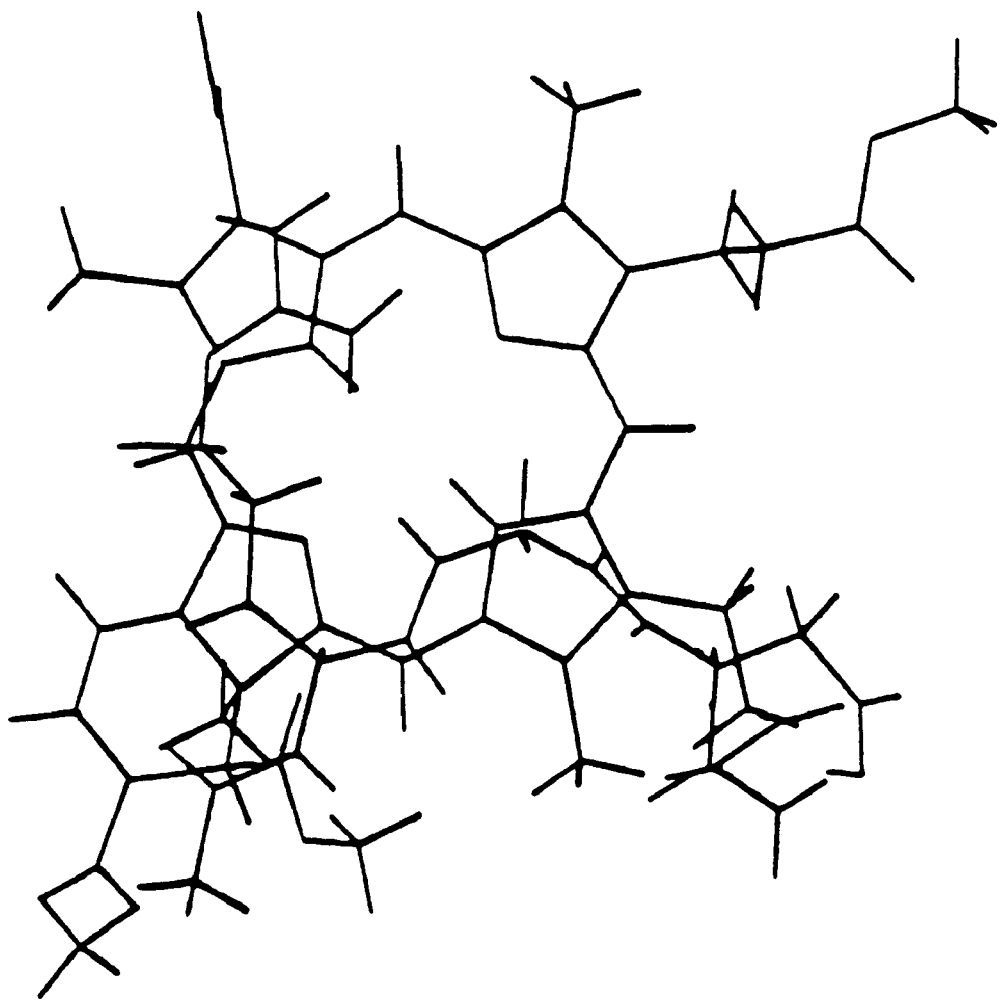
FIG. 7 shows the superimposition of the three-dimensional structure of BPD-MA with a representative conformation of RGDC.

The conformations included within these families are shown superimposed in FIGS. 2–4: FIG. 2 shows RGDA; FIG. 3 shows RGDB; FIG. 4 shows RGDC. All conformations have a carboxylic acid (Asp) to nitrogen (Arg) functional group distance of 12–13 Å. FIGS. 5–7 show superimposed representative conformations of each of these three groups with BPD-MA. FIG. 5 represents BPD superimposed onto RGDA; FIG. 6 represents BPD-MA superimposed onto RGDB FIG. 7 shows BPD-MA superimposed onto RGDC.

In all of these superimpositions, the superimposed structures are flat and the functional groups of aspartic and arginine are superimposed onto the corresponding carboxylic acid and nitrogen functional groups of BPD-MA.

The results show that bpd appears to have several arrangements of functional groups that would mimic the conformations of integrin binding compounds.

What is claimed is:

1. A method to modulate an antigen-specific immune response which method comprises administering to a subject in need of such modulation, an amount of green porphyrin effective to modulate said immune response to the antigen in the absence of radiation absorbed by the green porphyrin, said administering being performed during the ongoing antigen-specific immune response to said antigen, wherein said circumstance of absence of radiation absorbed by the green porphyrin consists of exposure to ambient light.

2. The method of claim 1 wherein said green porphyrin is administered systemically in a liposomal composition.

3. The method of claim 1 wherein said antigen is an autoantigen.

4. The method of claim 1 wherein said subject is a recipient of foreign tissue.

5. The method of claim 1 wherein said antigen is associated with psoriasis.

6. The method of claim 1 wherein said antigen is an allergen.

7. The method of claim 1 wherein said green porphyrin is of a formula selected from the group consisting of:

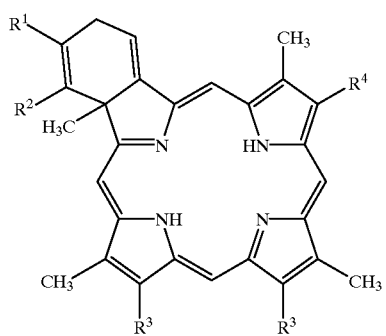

1

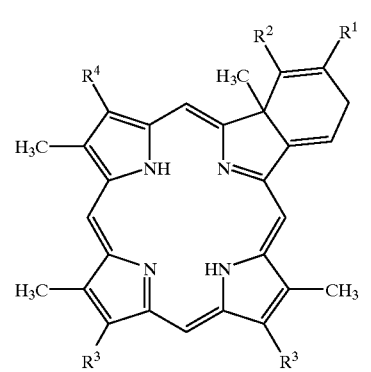

2

-continued

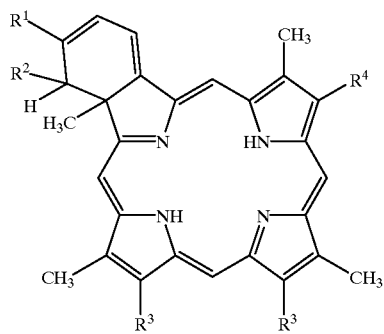

3

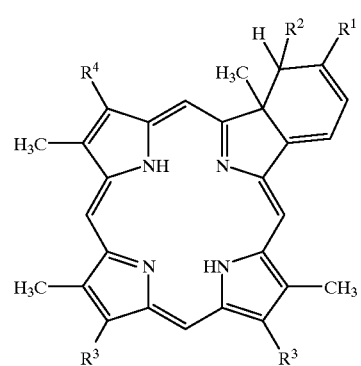

4

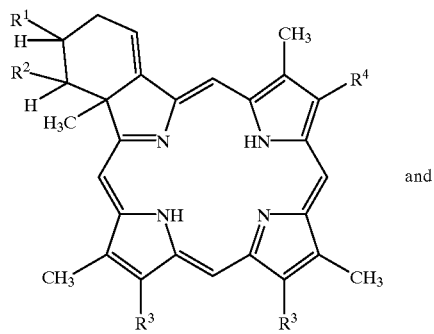

and

5

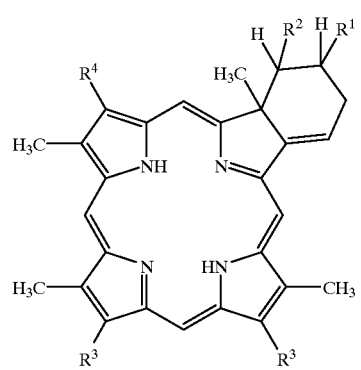

6 or a mixture thereof, wherein each of $R^1$ and $R^2$ in independently selected from the group consisting of carbalkoxyl (2–6C), alkyl (1–6C), arylsulfonyl (6–10C), cyano, and —CONR$^5$CO wherein $R^5$ is aryl (6–10) or alkyl (1–6C);

each $R^3$ is independently carboxyl, carboxyalkyl (2–6C) or a salt, amide, ester or acylhydrazone or is alkyl (1–6C); and $R^4$ is —CH=CH$_2$ or —CH(OR$^{4'}$)CH$_3$ wherein $R^{4'}$ is H or alkyl (1–6C), optionally substituted with a hydrophilic substituent.

8. The method of claim 7 wherein said green porphyrin is of formula 3 or 4 or a mixture thereof and wherein each of $R^1$ and $R^2$ is independently carbalkoxyl (2–6C);

one $R^3$ is carboxyalkyl (2–6C) and the other $R^3$ is the ester of a carboxyalkyl (2–6C) substituent; and $R^4$ is —CH=CH$_2$ or —CH(OH)CH$_3$.

9. The method of claim 8 wherein said green porphyrin is of formula 3 and wherein $R^1$ and $R^2$ are methoxycarbonyl;

one $R^3$ is —CH$_2$CH$_2$COOCH$_3$ and the other $R^3$ is —CH$_2$CH$_2$COOH; and $R^4$ is —CH=CH$_2$.

10. A method to inhibit thrombosis which method comprises administering to a subject an amount of green porphyrin that is effective to inhibit formation of a clot in the absense of radiation absorbed by the green porphyrin, wherein said circumstance of absence of radiation absorbed by the green porphyrin consists of exposure to ambient light.

11. The method of claim 10 wherein said green porphyrin is administered systemically in a liposomal composition.

12. The method of claim 11 wherein said green porphyrin is of a formula selected from the group consisting of:

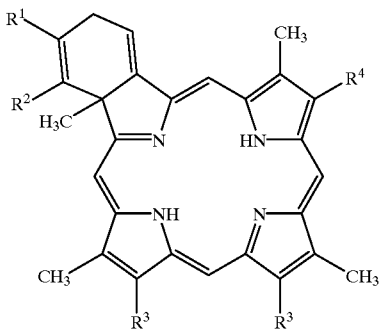

1

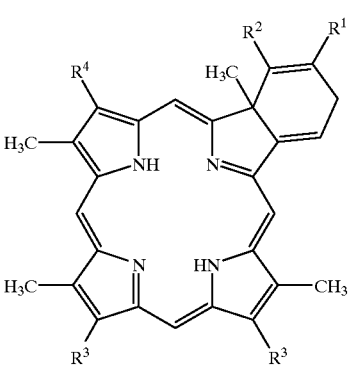

2

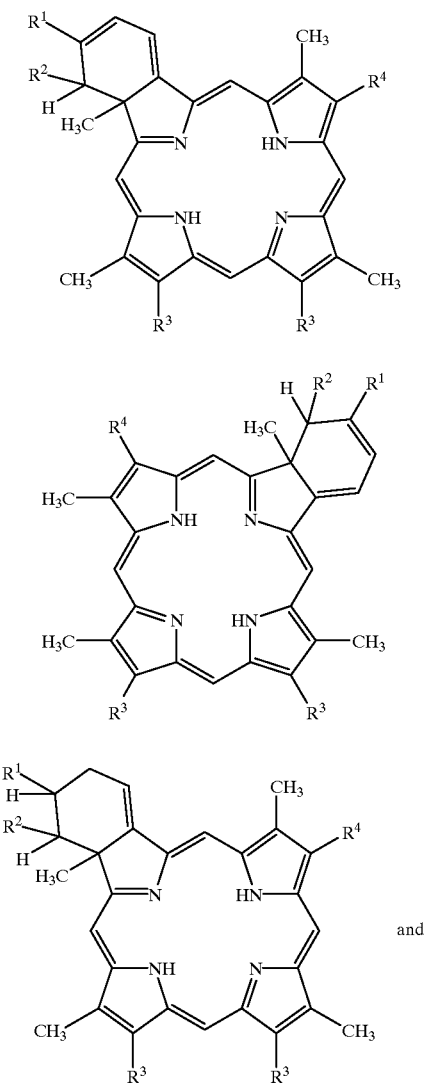

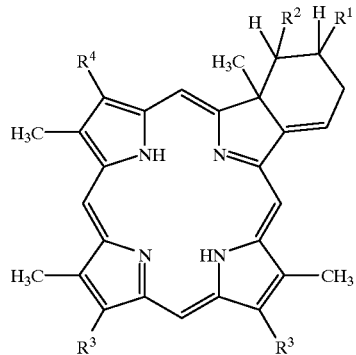

or a mixture thereof, wherein each of $R^1$ and $R^2$ in independently selected from the group consisting of carbalkoxyl (2–6C), alkyl (1–6C), arylsulfonyl (6–10C), cyano, and —$CONR^5CO$ wherein $R^5$ is aryl (6–10) or alkyl (1–6C);

each $R^3$ is independently carboxyl, carboxyalkyl (2–6C) or a salt, amide, ester or acylhydrazone or is alkyl (1–6C); and $R^4$ is —CH=$CH_2$ or —CH($OR^{4'}$)$CH_3$ wherein $R^{4'}$ is H or alkyl (1–6C), optionally substituted with a hydrophilic substituent.

13. The method of claim 12 wherein said green porphyrin is of the formula 1–3 or 1–4 or a mixture thereof and wherein each of $R^1$ and $R^2$ is independently carbalkoxyl (2–6C);

one $R^3$ is carboxyalkyl (2–6C) and the other $R^3$ is the ester of a carboxyalkyl (2–6C) substituent; and $R^4$ is —CH=$CH_2$ or —CH(OH)$CH_3$.

14. The method of claim 13 wherein said green porphyrin is of formula 3 and wherein $R^1$ and $R^2$ are methoxycarbonyl;

one $R^3$ is —$CH_2CH_2COOCH_3$ and the other $R^3$ is —$CH_2CH_2COOH$; and $R^4$ is —CH=$CH_2$.

* * * * *